(12) United States Patent
Kimura (10) Patent No.: US 7,612,349 B2
(45) Date of Patent: Nov. 3, 2009

(54) SURFACE PLASMON ENHANCED FLUORESCENCE SENSOR

(75) Inventor: Toshihito Kimura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 40 days.

(21) Appl. No.: 12/049,594

(22) Filed: Mar. 17, 2008

(65) Prior Publication Data
US 2008/0302975 A1  Dec. 11, 2008

(30) Foreign Application Priority Data
Mar. 15, 2007  (JP)  .............................. 2007-065999

(51) Int. Cl.
*G01N 21/64*  (2006.01)
(52) U.S. Cl. .............. 250/458.1; 250/459.1; 250/461.1; 250/461.2
(58) Field of Classification Search .............. 250/458.1, 250/459.1, 461.1, 461.2
See application file for complete search history.

(56) References Cited

U.S. PATENT DOCUMENTS 5,926,284 A * 7/1999 Naya et al. ................... 356/445
7,456,972 B2 * 11/2008 Ke et al. ...................... 356/445
2002/0056816 A1 * 5/2002 Stark ......................... 250/493.1
2003/0099422 A1 * 5/2003 Beom et al. .................... 385/12

FOREIGN PATENT DOCUMENTS

| JP | 1078390 A | 3/1998 |
|----|-----------|--------|
| JP | 3562912 B2 | 6/2004 |

OTHER PUBLICATIONS

Fang Yu et al., "Surface Plasmon Field-Enhanced Fluorescence Spectroscopy Studies of the Interaction between an Antibody and Its Surface-Coupled Antigen", Analytical Chemistry, 2003, pp. 2610-2617, vol. 75.

* cited by examiner

*Primary Examiner*—David P Porta
*Assistant Examiner*—Mindy Vu
(74) *Attorney, Agent, or Firm*—Sughrue Mion, PLLC (57) ABSTRACT

Exciting light is irradiated through a dielectric material block toward an interface between the dielectric material block and a metal film formed on one surface of the dielectric material block, such that total reflection conditions may be satisfied. An intensity of analysis fluorescence produced by an analysis fluorescent substance, which is contained in a sample and produces the analysis fluorescence by being excited by an evanescent wave oozing out from the interface when the exciting light impinges upon the interface, is normalized in accordance with an intensity of reference fluorescence produced by a reference fluorescent substance, which has been located at a position for excitation by the exciting light.

18 Claims, 7 Drawing Sheets

SURFACE PLASMON ENHANCED FLUORESCENCE SENSOR

BACKGROUND OF THE INVENTION

1. Field of the Invention

This invention relates to a fluorescence sensor for detecting a specific substance, which is contained in a sample, by use of a fluorometric analysis technique. This invention particularly relates to a fluorescence sensor, in which surface plasmon enhancement is utilized.

2. Description of the Related Art

Heretofore, in fields of biological analyses, and the like, a fluorometric analysis technique has been used widely as an analysis technique, which has a high sensitivity and is easy to perform. The fluorometric analysis technique is the technique, wherein exciting light having a specific wavelength is irradiated to a sample expected to contain a substance to be detected, which substance is capable of producing fluorescence by being excited by the exciting light having the specific wavelength, wherein the fluorescence having thus been produced by the substance to be detected is detected, and wherein the presence of the substance to be detected is thereby confirmed. In cases where the substance to be detected is not a fluorescent substance, a technique has heretofore been conducted widely, wherein a specific binding substance, which has been labeled with a fluorescent substance and is capable of undergoing the specific binding with the substance to be detected, is brought into contact with the sample, wherein the fluorescence is detected in the same manner as that described above, and wherein the occurrence of the specific binding, i.e. the presence of the substance to be detected, is thereby confirmed.

Figure 2:
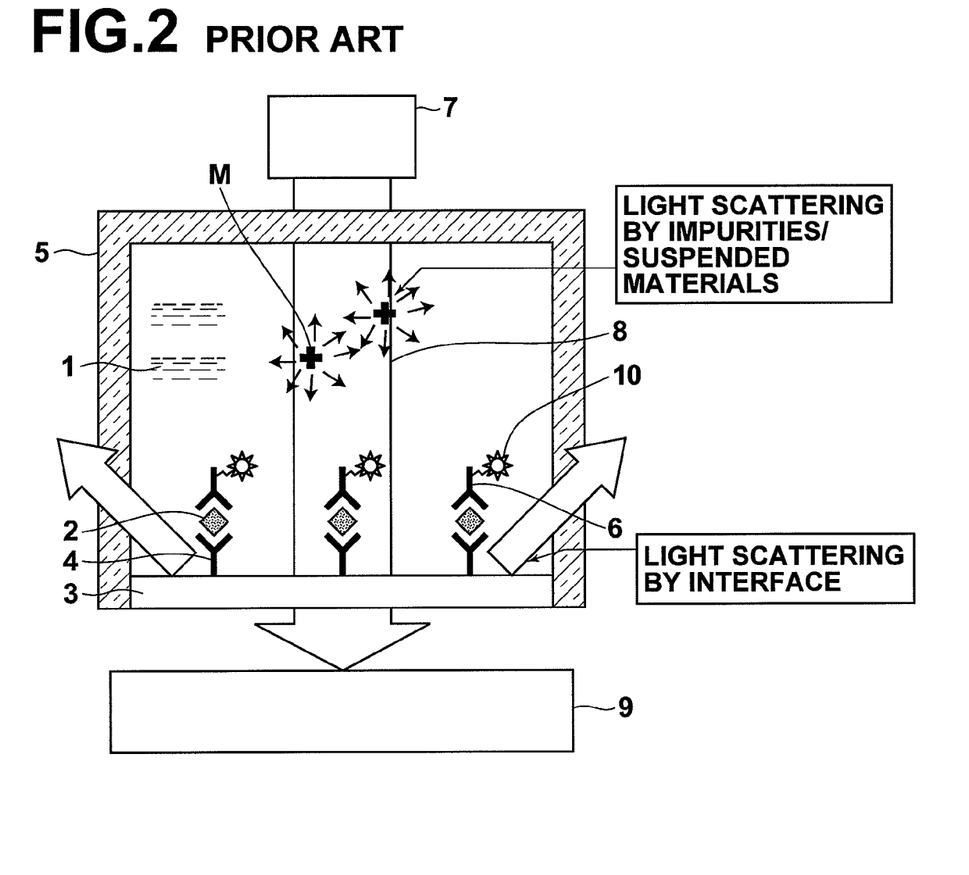
FIG. 2 is a schematic side view showing an example of a conventional fluorescence sensor for carrying out a fluorometric analysis technique utilizing a labeled specific binding substance.

FIG. 2 is a schematic side view showing an example of a conventional fluorescence sensor for carrying out a fluorometric analysis technique utilizing a labeled specific binding substance. By way of example, the fluorescence sensor illustrated in FIG. 2 is utilized for detecting an antigen 2, which is contained in a sample 1. The fluorescence sensor illustrated in FIG. 2 comprises a base plate 3, on which a primary antibody 4 capable of undergoing the specific binding with the antigen 2 has been coated. The fluorescence sensor also comprises a sample support section 5, which is formed on the base plate 3. The sample 1 is caused to flow within the sample support section 5. A secondary antibody 6, which has been labeled with a fluorescent substance 10 and is capable of undergoing the specific binding with the antigen 2, is then caused to flow within the sample support section 5. Thereafter, exciting light 8 is irradiated from an exciting light source 7 toward a surface area of the base plate 3. Also, an operation for detecting the fluorescence is performed by a photodetector 9. In cases where the predetermined fluorescence is detected by the photodetector 9, the specific binding of the secondary antibody 6 and the antigen 2 with each other, i.e. the presence of the antigen 2 in the sample, is capable of being confirmed.

In the example described above, the substance whose presence is actually confirmed with the fluorescence detecting operation is the secondary antibody 6. If the secondary antibody 6 does not undergo the specific binding with the antigen 2, the secondary antibody 6 will be carried away and will not be present on the base plate 3. Therefore, in cases where the presence of the secondary antibody 6 on the base plate 3 is detected, the presence of the antigen 2, which is the substance to be detected, is capable of being confirmed indirectly.

Particularly, with the rapid advances made in enhancement of performance of photodetectors, such as the advances made in cooled CCD image sensors, in recent years, the fluorometric analysis technique described above has become the means essential for biological studies. The fluorometric analysis technique has also been used widely in fields other than the biological studies. In particular, with respect to the visible region, as in the cases of FITC (fluorescence wavelength: 525 nm, quantum yield: 0.6), Cy5 (fluorescence wavelength: 680 nm, quantum yield: 0.3), and the like, fluorescent dyes having high quantum yields exceeding 0.2, which serves as a criterion for use in practice, have been developed. It is thus expected that the fields of the application of the fluorometric analysis technique will become wide even further.

However, with the conventional fluorescence sensor as illustrated in FIG. 2, the problems are encountered in that noise is caused to occur by the reflected/scattered exciting light at an interface between the base plate 3 and the sample 1 and the light scattered by impurities/suspended materials M, and the like, other than the substance to be detected. Therefore, with the conventional fluorescence sensor, even though the performance of the photodetectors is enhanced, it is not always possible to enhance the signal-to-noise ratio in the fluorescence detecting operation.

Figure 3:
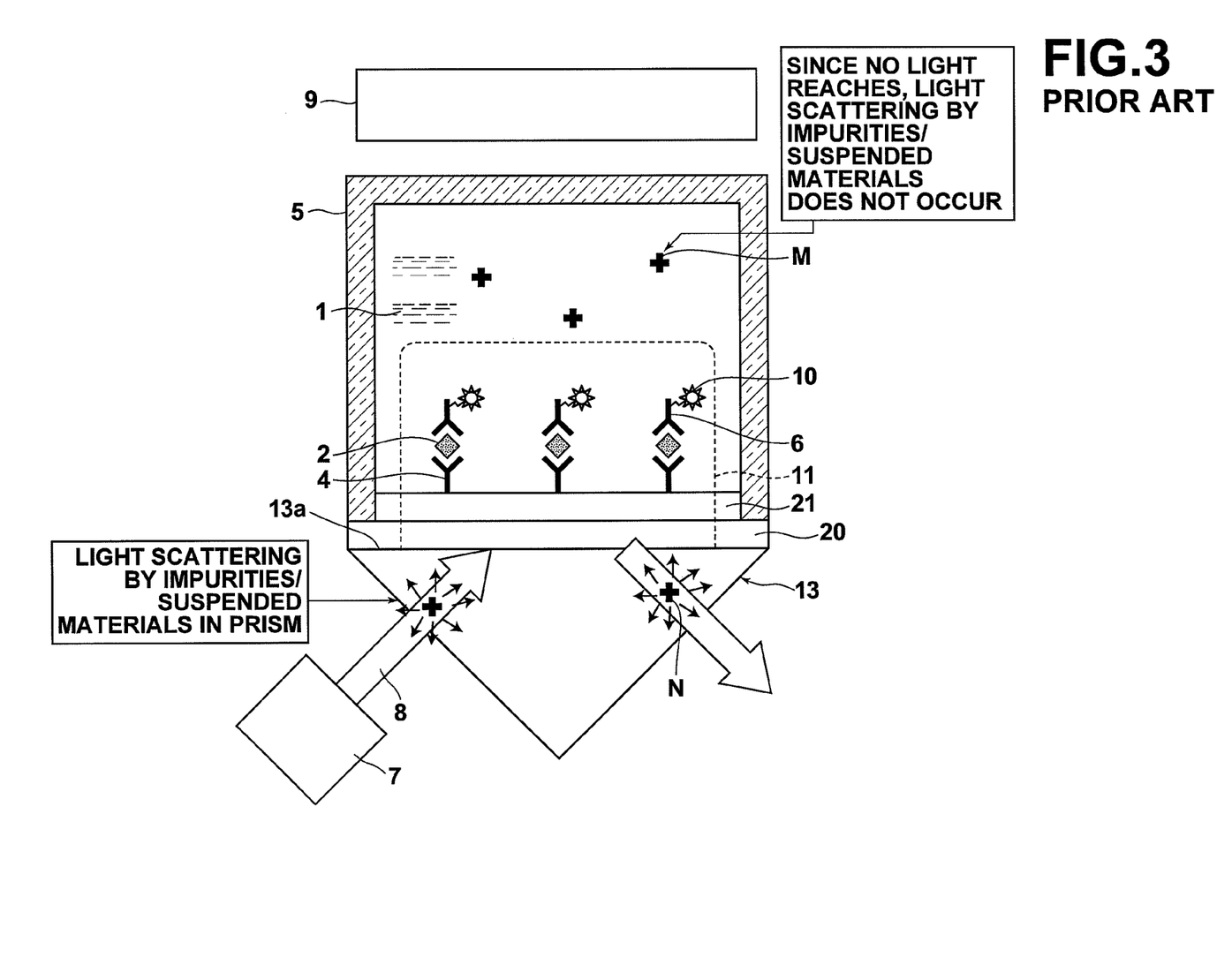
FIG. 3 is a schematic side view showing an example of a conventional fluorescence sensor for carrying out a fluorometric analysis technique utilizing an evanescent wave.

As a technique for solving the problems described above, a fluorometric analysis technique utilizing an evanescent wave has heretofore been proposed. FIG. 3 is a schematic side view showing an example of a conventional fluorescence sensor for carrying out a fluorometric analysis technique utilizing an evanescent wave. In FIG. 3 (and in FIG. 1, which will be described later), similar elements are numbered with the same reference numerals with respect to FIG. 2.

In the fluorescence sensor illustrated in FIG. 3, in lieu of the base plate 3 described above, a prism (a dielectric material block) 13 is utilized. A metal film 20 has been formed on a surface of the prism 13. Also, the exciting light 8 having been produced by the exciting light source 7 is irradiated through the prism 13 under the conditions such that the exciting light 8 may be totally reflected from the interface between the prism 13 and the metal film 20. With the constitution of the fluorescence sensor illustrated in FIG. 3, at the time at which the exciting light 8 is totally reflected from the interface described above, an evanescent wave 11 oozes out to the region in the vicinity of the interface described above, and the secondary antibody 6 is excited by the evanescent wave 11. Also, the fluorescence detecting operation is performed by the photodetector 9 located on the side of the sample 1, which side is opposite to the side of the prism 13. (In the cases of FIG. 3, the photodetector 9 is located on the upper side.)

With the fluorescence sensor illustrated in FIG. 3, the exciting light 8 is totally reflected from the aforesaid interface downwardly in FIG. 3. Therefore, in cases where the fluorescence detecting operation is performed from above, the problems do not occur in that an exciting light detection component constitutes the background with respect to a fluorescence detection signal. Also, the evanescent wave 11 is capable of reaching only a region of several hundreds of nanometers from the aforesaid interface. Therefore, the scattering from the impurities/suspended materials M contained in the sample 1 is capable of being suppressed. Accordingly, the evanescent fluorometric analysis technique described above has attracted particular attention for serving as a technique, which is capable of markedly suppressing (light) noise than with the conventional fluorometric analysis techniques, and with which the substance to be detected is capable of being fluorometrically analyzed in units of one molecule.

The fluorescence sensor illustrated in FIG. 3 is the surface plasmon enhanced fluorescence sensor, which has the sensitivity having been enhanced markedly among the fluorescence sensors utilizing the evanescent fluorometric analysis technique. With the surface plasmon enhanced fluorescence sensor, wherein the metal film 20 is formed, at the time at which the exciting light 8 is irradiated through the prism 13, the surface plasmon arises in the metal film 20, and the fluorescence is amplified by the electric field amplifying effect of the surface plasmon. A certain simulation has revealed that the fluorescence intensity in the cases described above is amplified by a factor of approximately 1,000. The surface plasmon enhanced fluorescence sensor of the type described above is described in, for example, Japanese Patent No. 3562912 and Japanese Unexamined Patent Publication No. 10 (1998)-078390.

In the cases of the surface plasmon enhanced fluorescence sensor, as described in, for example, a literature of F. Yu, et al., "Surface Plasmon Field-Enhanced Fluorescence Spectroscopy Studies of the Interaction between an Antibody and Its Surface-Coupled Antigen", Analytical Chemistry, Vol. 75, pp. 2610-2617, 2003, the problems occur in that, if the fluorescent substance contained in the sample and the metal film are markedly close to each other, energy having been excited in the fluorescent substance will undergo transition to the metal film before causing the fluorescent substance to produce the fluorescence, and a phenomenon of fluorescence production failure (i.e., the so-called metal quenching) will thus arise. In the literature described above, in order to cope with the metal quenching described above, a technique is proposed, wherein a self-organizing film (SAM) is formed on the metal film, and wherein the fluorescent substance contained in the sample and the metal film are spaced away from each other by a distance equal to at least the thickness of the SAM. In FIG. 3, the SAM is represented by the reference numeral 21.

With the surface plasmon enhanced fluorescence sensor described above, the fluorescence is amplified with the electric field amplifying effect of the surface plasmon, and the fluorescence, which represents the presence of the substance to be detected, is capable of being detected with a high signal-to-noise ratio. However, with the surface plasmon enhanced fluorescence sensor described above, new problems due to the presence of the metal film are encountered. Specifically, in the cases of the aforesaid type of the metal film, which is formed to a markedly small thickness, differences among individual metal films and intra-plane variations are apt to occur in thickness, composition, surface roughness, and the like. Therefore, the problems are encountered in that the intensity of the fluorescence detected fluctuates due to the differences among the individual metal films, and accordingly the accuracy of the measured value obtained from the quantitative analysis is not capable of being kept high.

SUMMARY OF THE INVENTION

The primary object of the present invention is to provide a surface plasmon enhanced fluorescence sensor, with which a quantitative analysis of a substance to be detected is capable of being made accurately regardless of differences among individual metal films.

The present invention provides a surface plasmon enhanced fluorescence sensor, in which, besides fluorescence representing the presence of a substance to be detected, reference fluorescence having been produced by a fluorescent substance for producing the reference fluorescence is detected, and in which the intensity of the fluorescence representing the presence of a substance to be detected is normalized in accordance with the intensity of the reference fluorescence. Specifically, the present invention provides a surface plasmon enhanced fluorescence sensor, comprising:

i) an exciting light source, which produces exciting light having a predetermined wavelength $\lambda_1$, ii) a dielectric material block, which has been formed from a material capable of transmitting the exciting light, iii) a metal film, which has been formed on one surface of the dielectric material block, iv) a sample support section for supporting a sample at a position in the vicinity of the metal film, v) an exciting light irradiating optical system for irradiating the exciting light through the dielectric material block toward an interface between the dielectric material block and the metal film, such that total reflection conditions may be satisfied, and vi) analysis fluorescence detecting means for detecting an intensity of analysis fluorescence having a wavelength $\lambda_2$ and having been produced by an analysis fluorescent substance, which is contained in the sample, the analysis fluorescent substance producing the analysis fluorescence by being excited by an evanescent wave oozing out from the interface at the time at which the exciting light has impinged upon the interface, wherein the improvement comprises the provision of:

a) a reference fluorescent substance, which is different from the analysis fluorescent substance and has been located at a position for excitation by the exciting light, b) reference fluorescence detecting means for detecting an intensity of reference fluorescence having a wavelength $\lambda_3$ and having been produced by the reference fluorescent substance, where $\lambda_3 \neq \lambda_2$, and c) operation processing means for normalizing the intensity of the analysis fluorescence, which has been detected by the analysis fluorescence detecting means, in accordance with the intensity of the reference fluorescence, which has been detected by the reference fluorescence detecting means.

In the surface plasmon enhanced fluorescence sensor in accordance with the present invention, the reference fluorescent substance may be located at the position for excitation by the exciting light before the exciting light impinges upon the interface between the dielectric material block and the metal film. Alternatively, the reference fluorescent substance may be located at the position for excitation by the evanescent wave of the exciting light, which has been radiated out from the interface.

Also, the surface plasmon enhanced fluorescence sensor in accordance with the present invention should preferably be modified such that single common photo detecting means is used as the analysis fluorescence detecting means and the reference fluorescence detecting means, and the surface plasmon enhanced fluorescence sensor further comprises:

a first filter for transmitting the analysis fluorescence having the wavelength $\lambda_2$ and blocking the reference fluorescence having the wavelength $\lambda_3$, a second filter for blocking the analysis fluorescence having the wavelength $\lambda_2$ and transmitting the reference fluorescence having the wavelength $\lambda_3$, and filter changeover means, which is capable of selectively locating either one of the first filter and the second filter at a stage previous to the single common photo detecting means.

Alternatively, the surface plasmon enhanced fluorescence sensor in accordance with the present invention may be modified such that two independent photo detecting means are used as the analysis fluorescence detecting means and the reference fluorescence detecting means, and the surface plasmon enhanced fluorescence sensor further comprises an optical element for causing the analysis fluorescence having the wavelength $\lambda_2$ to travel toward the analysis fluorescence detecting means, and causing the reference fluorescence having the wavelength $\lambda_3$ to travel toward the reference fluorescence detecting means.

In order for the reference fluorescence having the wavelength $\lambda_3$ to be obtained, the surface plasmon enhanced fluorescence sensor in accordance with the present invention may be modified such that, for example, a binding substance, which is capable of undergoing binding with a specific substance contained in the sample, has been fixed to a surface of the metal film, and the reference fluorescent substance has been fixed to the binding substance having been fixed to the surface of the metal film.

In such cases, by way of example, the binding substance, which is capable of undergoing the binding with the specific substance contained in the sample, may be an antibody, which is capable of undergoing the binding with an antigen contained in the sample.

Alternatively, in order for the reference fluorescence having the wavelength $\lambda_3$ to be obtained, the surface plasmon enhanced fluorescence sensor in accordance with the present invention may be modified such that the reference fluorescent substance has been fixed to a region of the dielectric material block.

As another alternative, in order for the reference fluorescence having the wavelength $\lambda_3$ to be obtained, the surface plasmon enhanced fluorescence sensor in accordance with the present invention may be modified such that a specific film has been formed on a surface of the metal film, and the reference fluorescent substance has been fixed to the specific film.

In such cases, the specific film may be an inflexible film constituted of a hydrophobic material.

As a further alternative, in order for the reference fluorescence having the wavelength $\lambda_3$ to be obtained, the surface plasmon enhanced fluorescence sensor in accordance with the present invention may be modified such that the reference fluorescent substance has been mixed in the sample (which may be, for example, in a liquid state).

Furthermore, the surface plasmon enhanced fluorescence sensor in accordance with the present invention may be modified such that the fluorescence, which is produced by the reference fluorescent substance through multiphoton absorption, is employed as the reference fluorescence.

With the surface plasmon enhanced fluorescence sensor in accordance with the present invention, the intensity of the reference fluorescence, which has been produced by the reference fluorescent substance when the reference fluorescent substance is excited by the exciting light, is detected, and the intensity of the analysis fluorescence, which has been detected by the analysis fluorescence detecting means, is normalized in accordance with the detected intensity of the reference fluorescence. Therefore, with the surface plasmon enhanced fluorescence sensor in accordance with the present invention, in cases where differences among individual metal films and intra-plane variations occur in thickness, composition, surface roughness, and the like, the normalized analysis fluorescence intensity is capable of canceling the differences among individual metal films and is capable of accurately representing the quantity of the substance to be detected, which is contained in the sample.

As described above, with the surface plasmon enhanced fluorescence sensor in accordance with the present invention, the differences among the individual metal films are allowed to occur, and the substance to be detected is capable of being detected quantitatively. Therefore, with the surface plasmon enhanced fluorescence sensor in accordance with the present invention, the parts of the dielectric material block and the metal film are capable of being constituted in disposable forms with a low cost, and a simple analysis apparatus for domestic use, or the like, is capable of being constituted easily.

Also, with the surface plasmon enhanced fluorescence sensor in accordance with the present invention, wherein the inflexible film constituted of the hydrophobic material is formed on the surface of the metal film, and wherein the reference fluorescent substance has been fixed to the inflexible film, the problems are capable of being prevented from occurring in that the analysis fluorescent substance contained in the sample liquid is located close to the metal film such that the metal quenching may occur. Therefore, in such cases, the metal quenching described above is not caused to occur. Accordingly, the electric field amplifying effect with the surface plasmon is capable of being obtained reliably, and the fluorescence detecting operation is capable of being performed with a markedly high sensitivity.

Further, with the surface plasmon enhanced fluorescence sensor in accordance with the present invention, wherein the inflexible film is made from the hydrophobic material, the problems do not occur in that the molecules, which will cause the quenching to occur, such as metal ions and dissolved oxygen present in the sample liquid, enter into the interior of the inflexible film. Therefore, the problems are capable of being prevented from occurring in that the molecules described above deprive the exciting light of the excitation energy. Accordingly, in such cases, a markedly high level of excitation energy is capable of being obtained, and the fluorescence detecting operation is capable of being performed with a markedly high sensitivity.

The term "inflexible film" as used herein means the film, which has the rigidity to an extent such that the film may not be deformed to a different film thickness during the ordinary use of the sensor.

Furthermore, with the surface plasmon enhanced fluorescence sensor in accordance with the present invention, in cases where the reference fluorescent substance is located in the enhancement field, up-conversion fluorescence occurring due to the multiphoton absorption is capable of being detected as the reference fluorescence. Therefore, with the surface plasmon enhanced fluorescence sensor in accordance with the present invention, wherein the up-conversion fluorescence occurring due to the multiphoton absorption is obtained as the reference fluorescence, the reference fluorescence having a large difference in wavelength from the analysis fluorescence is capable of being detected. Accordingly, the reference fluorescence and the analysis fluorescence are capable of being clearly discriminated from each other and are capable of being detected accurately.

DESCRIPTION OF THE PREFERRED EMBODIMENTS

The present invention will hereinbelow be described in further detail with reference to the accompanying drawings.

Figure 1:
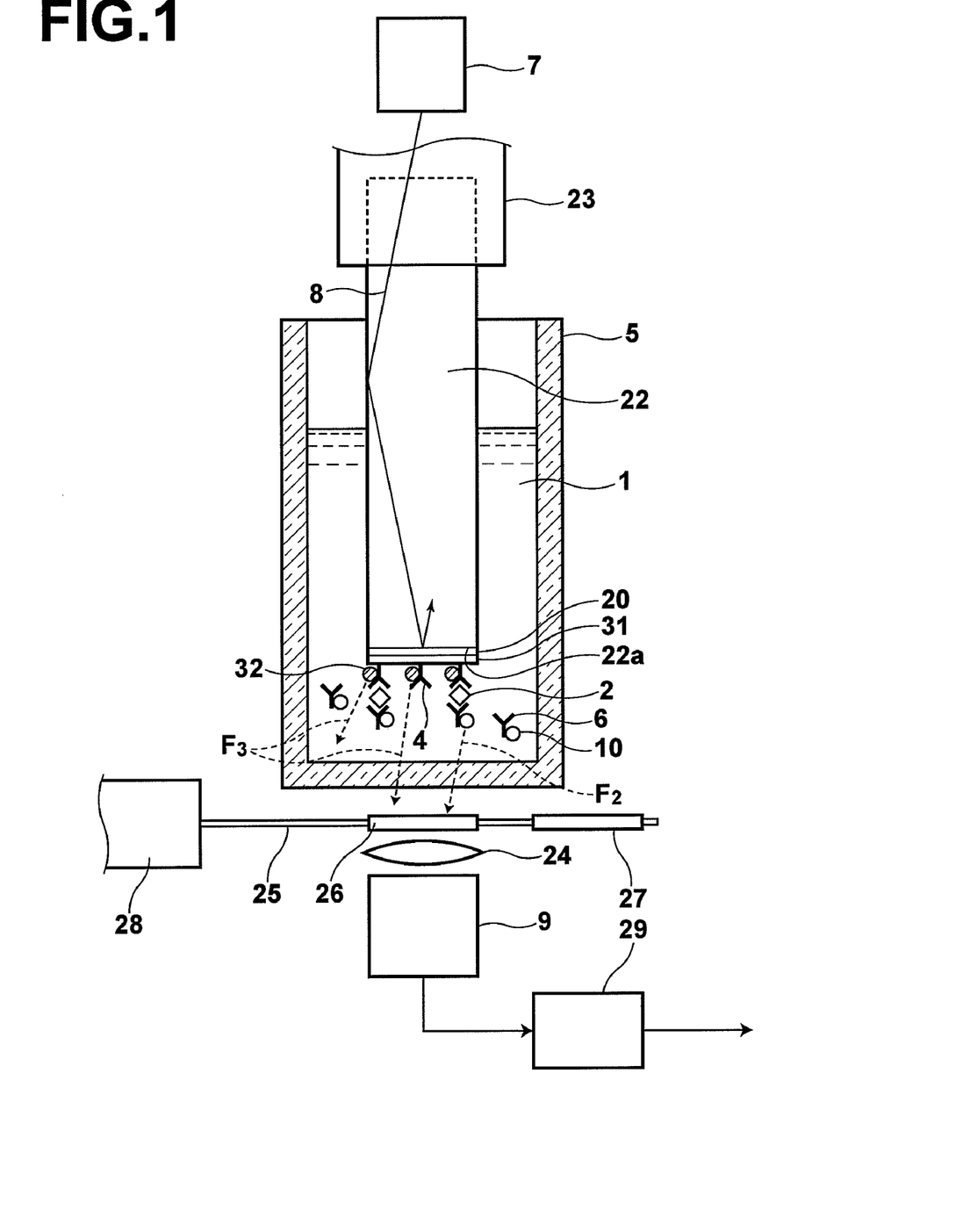
FIG. 1 is a schematic side view showing a first embodiment of the surface plasmon enhanced fluorescence sensor in accordance with the present invention.

FIG. 1 is a schematic side view showing a first embodiment of the surface plasmon enhanced fluorescence sensor in accordance with the present invention. (The surface plasmon enhanced fluorescence sensor will hereinbelow be referred to simply as the fluorescence sensor.) As illustrated in FIG. 1, the fluorescence sensor comprises an exciting light source 7, such as a semiconductor laser, for producing exciting light 8 having a wavelength $\lambda_1$ of, for example, 670 nm. The fluorescence sensor also comprises a rod-shaped dielectric material block 22, which is made from a material capable of transmitting the exciting light 8. The dielectric material block 22 is located such that the exciting light 8 having been produced by the exciting light source 7 may enter from a top end face of the dielectric material block 22 into the interior of the dielectric material block 22. The fluorescence sensor further comprises a metal film 20, which has been formed on one surface 22a of the dielectric material block 22. The fluorescence sensor still further comprises an inflexible film 31, which has been formed on the metal film 20 and which is constituted of a polymer. The fluorescence sensor also comprises a sample support section 5 for supporting a liquid-state sample 1 such that the sample 1 may be brought into contact with the inflexible film 31. The sample support section 5 is constituted of a transparent member. The fluorescence sensor further comprises a chuck 23 for supporting the dielectric material block 22 within the sample support section 5.

The fluorescence sensor still further comprises a photodetector 9, which is located at a position under the sample support section 5 so as to stand facing the metal film 20. The fluorescence sensor also comprises a converging lens 24, which is located between the photodetector 9 and the sample support section 5. The fluorescence sensor further comprises a first filter 26 and a second filter 27, which are supported by a filter support member 25. The fluorescence sensor still further comprises an actuator 28 for moving the filter support member 25 in the horizontal directions in FIG. 1. The fluorescence sensor also comprises an operation processing circuit 29 for receiving outputs from the photodetector 9.

In this embodiment, the exciting light source 7 is located for irradiating the exciting light 8 through the dielectric material block 22 toward the interface between the dielectric material block 22 and the metal film 20, such that the total reflection conditions may be satisfied. Specifically, the exciting light source 7 by itself constitutes the exciting light irradiating optical system for irradiating the exciting light 8 in the manner described above with respect to the dielectric material block 22. However, the fluorescence sensor in accordance with the present invention is not limited the constitution described above. For example, alternatively, an irradiating optical system, which comprises a lens, a mirror, and the like, for irradiating the exciting light 8 in the manner described above, may be located as an independent system besides the exciting light source 7.

By way of example, the dielectric material block 22 may be constituted of ZEONEX (trade name) 330R (refractive index: 1.50), supplied by Nippon Zeon Co., Ltd. The metal film 20 has been formed with processing, in which gold is formed on the one surface 22 of the dielectric material block 22 by use of a sputtering technique. The film thickness of the metal film 20 is set at 50 nm. Also, the inflexible film 31 has been formed with processing, in which a polystyrene type polymer having a refractive index of 1.59 is formed on the metal film 20 by use of a spin coating technique. The film thickness of the inflexible film 31 is set at 20 nm.

Besides the material described above, the dielectric material block 22 may be formed by use of a known resin, a known optical glass, or the like. From the view point of the cost, the resin is more preferable than the optical glass. In cases where the dielectric material block 22 is to be made from a resin, the resin may be selected appropriately from a polymethyl methacrylate (PMMA), a polycarbonate (PC), an amorphous polyolefin (APO) containing a cycloolefin, and the like.

By way of example, the object of the detection with the embodiment of the fluorescence sensor is a CRP antigen 2 (molecular weight: 110,000 Da). A primary antibody (a monoclonal antibody) 4, which is capable of undergoing the specific binding with the CRP antigen 2, has been fixed to the inflexible film 31. The primary antibody 4 has been fixed to the inflexible film 31, which is constituted of a polymer, via, for example, PEG having a terminal introduced with a carboxyl group, by use of an amine coupling technique. Also, a fluorescent dye (acting as a reference fluorescent substance) 32 has been fixed to the primary antibody 4 having been fixed to the inflexible film 31. The fluorescent dye 32 has the characteristics such that the fluorescent dye 32 produces fluorescence (reference fluorescence) $F_3$ having a peak wavelength $\lambda_3$ of 780 nm when being excited by the exciting light 8 having the wavelength $\lambda_1$ of 670 nm. Specifically, Cy7 is employed as the fluorescent dye 32.

At the time at which the fluorescence detecting operation is to be performed, a secondary antibody 6 is mixed in the sample 1. As the secondary antibody 6, for example, a monoclonal antibody, which has been labeled with a fluorescent substance 10, such as rhodamine B, is employed. (The monoclonal antibody employed as the secondary antibody 6 varies in epitope (antigenic determinant) from the primary antibody 4.) The fluorescent substance (acting as the analysis fluorescent substance) 10 has the characteristics such that the fluorescent substance 10 produces fluorescence (analysis fluorescence) $F_2$ having a peak wavelength $\lambda_2$ of 720 nm when being excited by the exciting light 8 having the wavelength $\lambda_1$ of 670 nm (Alexa700).

By way of example, the aforesaid amine coupling technique comprises the steps (1), (2), and (3) described below. The example described below is of the cases wherein a 30 μl (microliter) cuvette/cell is used.

(1) Activation of a —COOH Group at a Linker End (Terminal)

A solution, which has been prepared by mixing 0.1M (mol) NHS and 0.4M EDC together in an equal volume ratio, is added in an amount of 30 μl, and the resulting mixture is allowed to stand for 30 minutes at the room temperature.

NHS: N-Hydrooxysuccinimide

EDC: 1-Ethyl-3-(3-dimethylaminopropyl)carbodiimide (2) Fixation of the Primary Antibody 4

After washing with a PBS buffer (pH7.4) is performed five times, a primary antibody solution (500 µg/ml) is added in an amount of 30 µl, and the resulting mixture is allowed to stand for 30 to 60 minutes at the room temperature.

(3) Blocking of an Unreacted —COOH Group

After washing with the PBS buffer (pH7.4) is performed five times, 1M ethanolamine (pH8.5) is added in an amount of 30 µl, and the resulting mixture is allowed to stand for 20 minutes at the room temperature. Washing with the PBS buffer (pH7.4) is then performed five times.

The exciting light source 7 is not limited to the semiconductor laser described above and may be selected from the other various kinds of the known light sources. Also, the fluorescence detecting means is not limited to the photodetector 9 described above and may be selected from the other various kinds of the known devices, such as a CCD, a PD (a photodiode), a photomultiplier, and c-MOS. Further, in cases where the excitation wavelength is altered, a dye other than rhodamine B is capable of being employed as a label.

As the photodetector 9, it is possible to employ, for example, LAS-1000 plus (trade name), supplied by Fuji Photo Film Co., Ltd. The photodetector 9 is capable of detecting both the analysis fluorescence $F_2$ having the peak wavelength $\lambda_2$ of 720 nm and the reference fluorescence $F_3$ having the peak wavelength $\lambda_3$ of 780 nm. Specifically, the photodetector 9 acts as both the analysis fluorescence detecting means and the reference fluorescence detecting means.

The first filter 26 having been supported by the filter support member 25 has the transmission characteristics such that the first filter 26 transmits the analysis fluorescence $F_2$ having the wavelengths falling within the range of 720±10 nm and blocks the reference fluorescence $F_3$ having the wavelengths falling within the range of 780±10 nm. Also, the second filter 27 having been supported by the filter support member 25 has the transmission characteristics such that the second filter 27 transmits the reference fluorescence $F_3$ and blocks the analysis fluorescence $F_2$.

How the embodiment of the fluorescence sensor operates will be described hereinbelow by taking the cases of the quantitative analysis of the CRP antigen 2, which is contained in the sample 1, as an example. Firstly, the liquid-state sample 1 is caused to flow within the sample support section 5. Thereafter, in the same manner, the secondary antibody 6, which has been labeled with the fluorescent substance 10 and which is capable of undergoing the specific binding with the CRP antigen 2, is caused to flow within the sample support section 5. Alternatively, instead of the liquid-state sample 1 being caused to flow within the sample support section 5 in the manner described above, the liquid-state sample 1 may be stored in the sample support section 5, and the fluorescence detecting operation may be performed in this state. As another alternative, in lieu of the sample support section 5 illustrated in FIG. 1 being provided, the region of the inflexible film 31 of the dielectric material block 22 may be brought into contact with the liquid-state sample 1 contained in a vessel and may thereafter be brought into contact with the secondary antibody 6 contained in a different vessel, and thereafter the dielectric material block 22 may be set at the fluorescence detecting system illustrated in FIG. 1 and may thus be subjected to the analysis operation.

At the time at which the fluorescence detecting operation is to be performed, firstly, the actuator 28 is operated, and the second filter 27 is located at the position which stands facing the converging lens 24. Thereafter, the exciting light 8 having the wavelength $\lambda_1$ of 670 nm is irradiated from the exciting light source 7 toward the dielectric material block 22. At this time, part of the exciting light 8 impinges upon the interface between the dielectric material block 22 and the metal film 20, such that the total reflection conditions may be satisfied. As a result, the evanescent wave having the identical wavelength oozes out from the interface. Therefore, the fluorescent dye 32 having been bound with the primary antibody 4 having been fixed to the inflexible film 31 is excited by the evanescent wave to produce the reference fluorescence $F_3$ having the peak wavelength $\lambda_3$ of 780 nm.

In cases where the secondary antibody 6 is present at the position in the vicinity of the inflexible film 31, the fluorescent substance 10 acting as the label of the secondary antibody 6 will be excited by the evanescent wave to produce the analysis fluorescence $F_2$ having the peak wavelength $\lambda_2$ of 720 nm. However, since the second filter 27 is located in the manner described above, the photodetector 9 detects only the reference fluorescence $F_3$. Also, a reference signal $P_3$, which represents the intensity of the reference fluorescence $F_3$, is outputted from the photodetector 9. The reference signal $P_3$ is temporarily stored in an internal memory of the operation processing circuit 29.

Thereafter, the actuator 28 is operated, and the first filter 26 is located at the position which stands facing the converging lens 24. At this time, in cases where the CRP antigen 2 has been bound with the primary antibody 4, the secondary antibody 6 undergoes the binding with the antigen 2, and the fluorescent substance 10 acting as the label of the secondary antibody 6 is excited by the evanescent wave described above. The fluorescent substance 10 having thus been excited by the evanescent wave produces the analysis fluorescence $F_2$ having the peak wavelength $\lambda_2$ of 720 nm. The analysis fluorescence $F_2$ is detected by the photodetector 9. At this time, the reference fluorescence $F_3$, which has the peak wavelength $\lambda_3$ of 780 nm and has been produced by the fluorescent dye 32, is blocked by the first filter 26 and is therefore not detected by the photodetector 9.

An analysis signal $P_2$, which represents the intensity of the analysis fluorescence $F_2$, is outputted from the photodetector 9. The analysis signal $P_2$ is fed into the operation processing circuit 29. In accordance with the analysis signal $P_2$ and the previously stored reference signal $P_3$, the operation processing circuit 29 makes a calculation with the formula $P=P_2/P_3$. The operation processing circuit 29 outputs the thus obtained signal P as a normalized fluorescence intensity signal.

As described above, as for the metal film 20, the differences among individual metal films often occur in thickness, composition, surface roughness, and the like. In such cases, the value of the analysis signal $P_2$, which represents the intensity of the analysis fluorescence $F_2$, fluctuates in accordance with the differences among the individual metal films. The analysis fluorescence intensity signal $P_2$ is the signal representing the value corresponding to the quantity of the fluorescent substance 10 having been excited, i.e. the quantity of the CRP antigen 2 having been bound with the primary antibody 4. In accordance with the analysis fluorescence intensity signal $P_2$, it is possible to make the quantitative analysis of the CRP antigen 2. However, if the analysis fluorescence intensity signal $P_2$ fluctuates in accordance with the differences among the individual metal films 20, 20, . . . , the accuracy of the quantitative analysis will be affected adversely. However, with this embodiment, wherein the normalizing operation processing represented by the formula $P=P_2/P_3$ is performed, it is possible to obtain the normalized fluorescence intensity signal P, which cancels the differences among the individual metal films 20, 20, . . . , and which accurately represents the quantity of the CRP antigen 2.

In cases where the quantitative analysis is capable of being made accurately with the differences among the individual metal films 20, 20, . . . being allowed to occur to a certain extent as described above, the parts of the dielectric material block 22 and the metal film 20 are capable of being constituted in disposable forms with a low cost, and a simple analysis apparatus for domestic use, or the like, is capable of being constituted easily.

The evanescent wave described above is capable of reaching only the region of approximately several hundreds of nanometers from the interface between the dielectric material block 22 and the metal film 20. Therefore, the scattering from the impurities/suspended materials contained in the sample 1 is capable of being eliminated approximately perfectly. Also, the light, which has been scattered by impurities contained in the dielectric material block 22, (which light is the ordinary propagated light) is blocked by the metal film 20 and does not impinge upon the photodetector 9. Accordingly, with this embodiment of the fluorescence sensor, the occurrence of light noise is capable of being eliminated approximately perfectly, and the fluorescence is capable of being detected with a markedly high signal-to-noise ratio.

Further, with this embodiment of the fluorescence sensor, wherein the inflexible film 31 having a film thickness of 20 nm is formed on the metal film 20, the problems are capable of being prevented from occurring in that the fluorescent substance 10 contained in the sample 1 becomes close to the metal film 20 to an extent such that the metal quenching may occur. Therefore, with this embodiment of the fluorescence sensor, the metal quenching described above is not caused to occur. Accordingly, the electric field amplifying effect with the surface plasmon is capable of being obtained reliably, and the fluorescence is capable of being detected with a markedly high sensitivity.

Furthermore, with this embodiment of the fluorescence sensor, wherein the inflexible film 31 is made from the polystyrene type polymer, which is the hydrophobic material, the problems do not occur in that the molecules, which will cause the quenching to occur, such as metal ions and dissolved oxygen present in the liquid-state sample 1, enter into the interior of the inflexible film 31. Therefore, the problems are capable of being prevented from occurring in that the molecules described above deprive the exciting light 8 of the excitation energy. Accordingly, with this embodiment of the fluorescence sensor, a markedly high level of excitation energy is capable of being obtained, and the fluorescence is capable of being detected with a markedly high sensitivity.

In this embodiment of the fluorescence sensor, the evanescent wave does not reach the secondary antibody 6, which has not been bound with the CRP antigen 2 and is spaced away from the surface of the inflexible film 31. Therefore, the secondary antibody 6, which has not been bound with the CRP antigen 2 and is spaced away from the surface of the inflexible film 31, does not produce the fluorescence. Accordingly, in cases where the secondary antibody 6 as described above is being suspended in the sample 1, no problems occur with respect to the measurement, and a washing operation, i.e. a B/F separating operation (a bound/free separating operation) need not be performed for each stage of the measurement.

A second embodiment of the fluorescence sensor in accordance with the present invention will be described hereinbelow with reference to FIG. 4. The second embodiment of the fluorescence sensor in accordance with the present invention is constituted basically in the same manner as that in the first embodiment of the fluorescence sensor of FIG. 1, except for the position at which the reference fluorescent substance for yielding the reference signal $P_3$ is located. Specifically, in the second embodiment, a region of the dielectric material block 22 close to the surface 22a of the dielectric material block 22, to which surface the metal film 20 is fixed, is formed from a fluorescent substance (acting as the reference fluorescent substance) 40.

With the constitution of the second embodiment of the fluorescence sensor in accordance with the present invention, the fluorescent substance 40 is excited by the exciting light 8 having the wavelength $\lambda_1$ to produce the reference fluorescence $F_3$ having the wavelength $\lambda_3$. The reference fluorescence $F_3$ passes through the metal film 20 and the inflexible film 31 and is detected by the photodetector 9. The reference fluorescence $F_3$ is thus utilized for the normalization in the same manner as that in the first embodiment described above. By way of example, the fluorescent substance 40 formed at the part of the dielectric material block 22 is capable of being formed with a two-color molding technique.

A third embodiment of the fluorescence sensor in accordance with the present invention will be described hereinbelow with reference to FIG. 5. The third embodiment of the fluorescence sensor in accordance with the present invention is constituted basically in the same manner as that in the first embodiment of the fluorescence sensor of FIG. 1, except for the position at which the reference fluorescent substance for yielding the reference signal $P_3$ is located. Specifically, in the third embodiment, an inflexible film 31a, which has been formed on the metal film 20, is constituted of a fluorescent substance (acting as the reference fluorescent substance).

With the constitution of the third embodiment of the fluorescence sensor in accordance with the present invention, in cases where the exciting light 8 having the wavelength $\lambda_1$ is irradiated toward the interface between the dielectric material block 22 and the metal film 20, the evanescent wave having the identical wavelength oozes out from the interface. The inflexible film 31a constituted of the fluorescent substance (acting as the reference fluorescent substance) is thus excited by the evanescent wave to produce the reference fluorescence $F_3$ having the wavelength $\lambda_3$. The reference fluorescence $F_3$ is detected by the photodetector 9. The reference fluorescence $F_3$ is thus utilized for the normalization in the same manner as that in the first embodiment described above.

With the third embodiment of the fluorescence sensor in accordance with the present invention, in the same manner as that in the first embodiment described above, for example, the exciting light wavelength $\lambda_1$ may be set at 670 nm. Also, the secondary antibody 6 may be labeled with rhodamine B, or the like, and the analysis fluorescence $F_2$ having the peak wavelength $\lambda_2$ of 720 nm may be produced from the label of the secondary antibody 6. Further, the reference fluorescence $F_3$ having the peak wavelength $\lambda_3$ of 780 nm may be produced from the inflexible film 31a.

A fourth embodiment of the fluorescence sensor in accordance with the present invention will be described hereinbelow with reference to FIG. 6. The fourth embodiment of the fluorescence sensor in accordance with the present invention is constituted basically in the same manner as that in the first embodiment of the fluorescence sensor of FIG. 1, except that a variable output circuit 41 is connected to the exciting light source 7, and except that the output of the exciting light source 7 is capable of being set at two levels E1 and E2. Also, a light source for producing the exciting light 8 having the wavelength $\lambda_1$ of 785 nm is employed as the exciting light source 7. Further, for example, FITC is employed as the fluorescent substance (acting as the reference fluorescent substance) 32 for labeling the primary antibody 4.

With the fourth embodiment of the fluorescence sensor, at the time at which the normalization data is to be obtained, the exciting light output of the exciting light source 7 is set at E2 higher than E1. The fluorescent substance 32 is thus caused to undergo two-photon absorption and is excited in the same manner as in the cases of the excitation with the exciting light having a wavelength of 785/2=393 nm. As a result, the fluorescent substance 32 produces the reference fluorescence $F_3$ having the wavelength $\lambda_3$ of 520 nm. Also, at the time of the ordinary fluorescence detecting operation, the exciting light output of the exciting light source 7 is set at E1. In cases where the exciting light output of the exciting light source 7 is set at the low output E1, a fluorescent dye (IRDye800CW) 10, which has been bound with the secondary antibody 6, is excited by the exciting light 8 having the wavelength $\lambda_1$ of 785 nm to produce the analysis fluorescence $F_2$ having the peak wavelength $\lambda_2$ of 790 nm. In this case, the difference between the value of the wavelength $\lambda_2$ and the value of the wavelength $\lambda_3$ is comparatively large. Therefore, in cases where filters, whose transmission characteristics are not markedly sharp, are employed as the first filter 26 and the second filter 27, the analysis fluorescence $F_2$ and the reference fluorescence $F_3$ are capable of being detected by being clearly discriminated from each other.

In cases where the reference fluorescence $F_3$ is produced through the two-photon excitation in the manner described above, the normalized fluorescence intensity signal P is capable of being calculated with the formula $P=P_2/(P_3)^{0.25}$, wherein $P_2$ represents the signal representing the intensity of the analysis fluorescence $F_2$, and $P_3$ represents the signal representing the intensity of the reference fluorescence $F_3$.

In cases where the fluorescent substance 32, which is to be caused to undergo the two-photon absorption, has been fixed to the primary antibody 4 and is located at a position markedly close to the metal film 20, there is the possibility that the fluorescent substance 32 will not produce the fluorescence due to the metal quenching. Therefore, such that the fluorescent substance 32 may be spaced sufficiently away from the metal film 20, the inflexible film 31 should preferably be constituted of a film of $SiO_2$, a polymer, or the like, having a thickness falling within the range of approximately 10 nm to approximately 20 nm.

Alternatively, FITC may be employed as the fluorescent dye 10 to be bound with the secondary antibody 6, and IRDye800CW may be employed as the fluorescent substance 32 for labeling the primary antibody 4. In such cases, the electric field amplifying effect with the surface plasmon becomes markedly large at the position of the secondary antibody 6. By the utilization of the characteristics described above, instead of the changeover between the exciting light output E1 and the exciting light output E2 being performed, the two-photon excitation is capable of being caused to occur only with the fluorescent dye 10. Specifically, with respect to the electric field amplifying effect described above, by way of example, in cases where a gold film having a thickness of 50 nm is employed as the metal film 20, and in cases where a self-organizing film (SAM) having a thickness of 1 nm is formed on the surface of the gold film described above, the presence of the secondary antibody 6 begins from the position at least approximately 35 nm spaced away from the surface of the metal film. Simulations performed by the inventors revealed that the electric field amplified by the surface plasmon takes the highest value at the position in the vicinity of the position at which the secondary antibody 6 is present.

Figure 7:
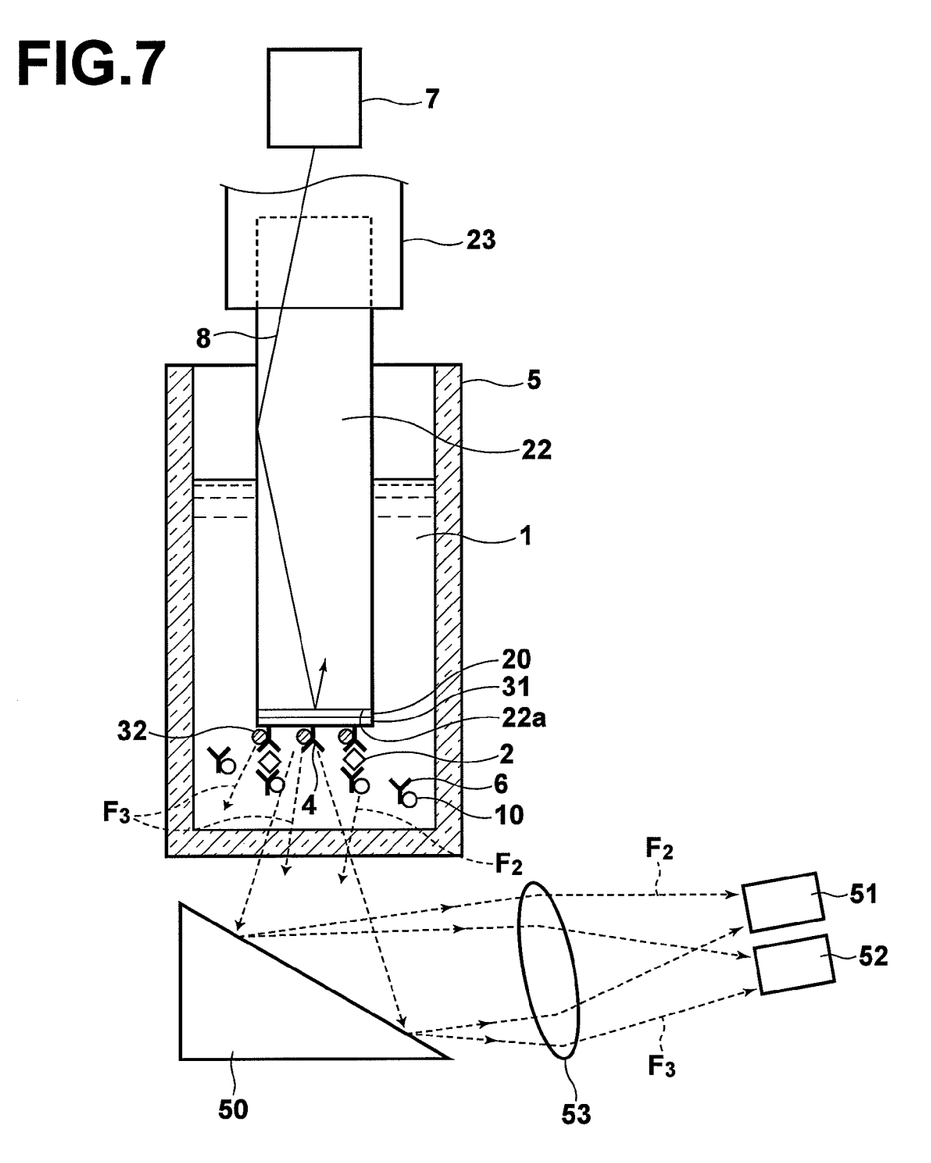
FIG. 7 is a schematic side view showing a fifth embodiment of the surface plasmon enhanced fluorescence sensor in accordance with the present invention.

A fifth embodiment of the fluorescence sensor in accordance with the present invention will be described hereinbelow with reference to FIG. 7. The fifth embodiment of the fluorescence sensor in accordance with the present invention is constituted basically in the same manner as that in the first embodiment of the fluorescence sensor of FIG. 1, except for a fluorescence detecting system located under the sample support section 5. Specifically, in the fifth embodiment, a diffraction grating 50 is located under the sample support section 5. Also, two photodetectors 51 and 52 are located along a side of the diffraction grating 50 via a converging lens 53.

The diffraction grating 50 reflects and diffracts the analysis fluorescence $F_2$ having the wavelength $\lambda_2$ and the reference fluorescence $F_3$ having the wavelength $\lambda_3$ at different diffraction angles. The analysis fluorescence $F_2$ and the reference fluorescence $F_3$, which thus travel in different directions, are converged by the converging lens 53 and are respectively received by the photodetector (the analysis fluorescence detecting means) 51, which has a sensitivity with respect to the wavelength range of the analysis fluorescence $F_2$, and the photodetector (the reference fluorescence detecting means) 52, which has a sensitivity with respect to the wavelength range of the reference fluorescence $F_3$. With the constitution of this embodiment, the detection of the analysis fluorescence $F_2$ and the detection of the reference fluorescence $F_3$ are capable of being performed at the same time, and therefore the operation efficiency of the fluorescence detecting operation is capable of being enhanced.

Figure 4:
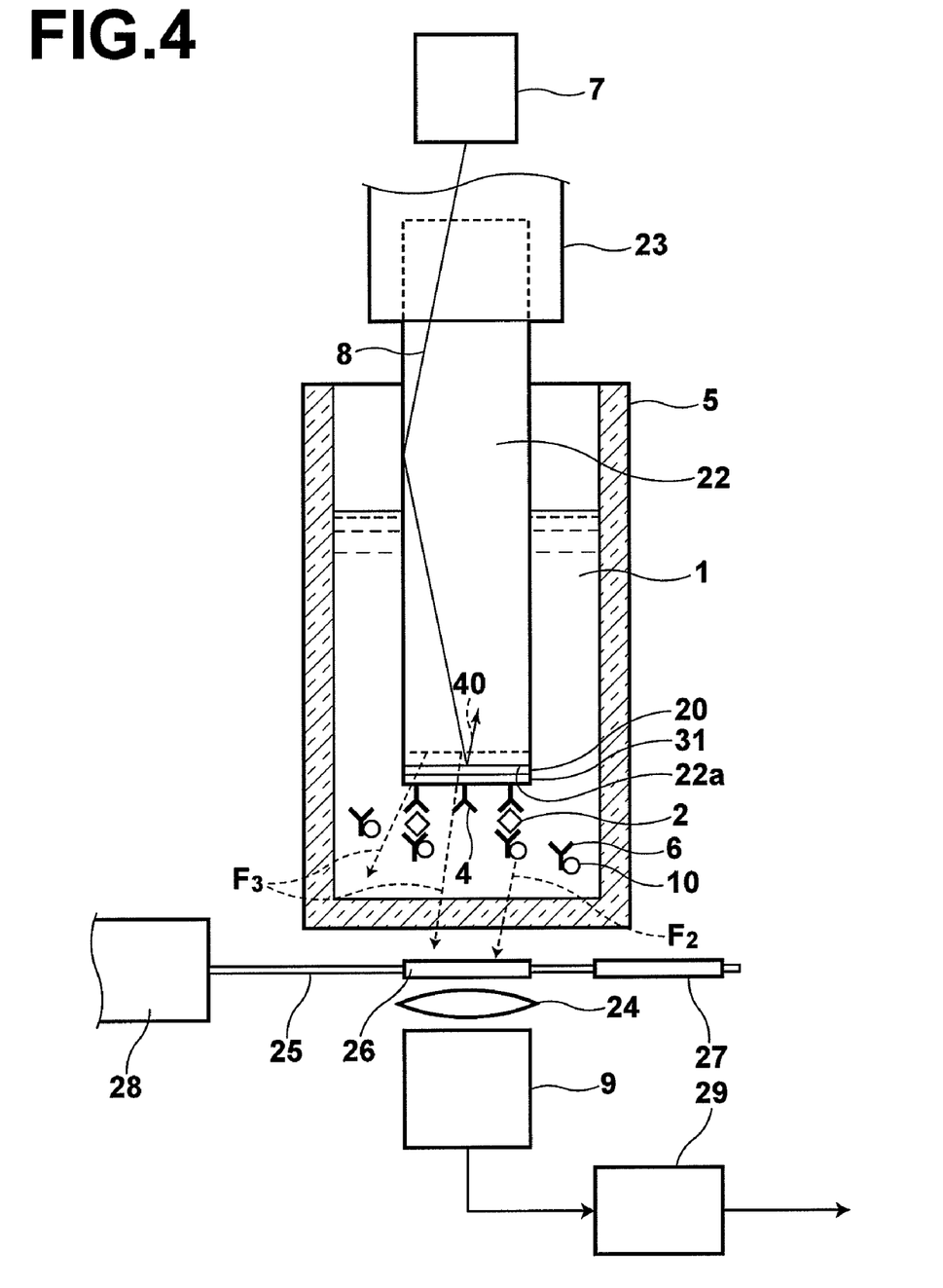
FIG. 4 is a schematic side view showing a second embodiment of the surface plasmon enhanced fluorescence sensor in accordance with the present invention.
Figure 5:
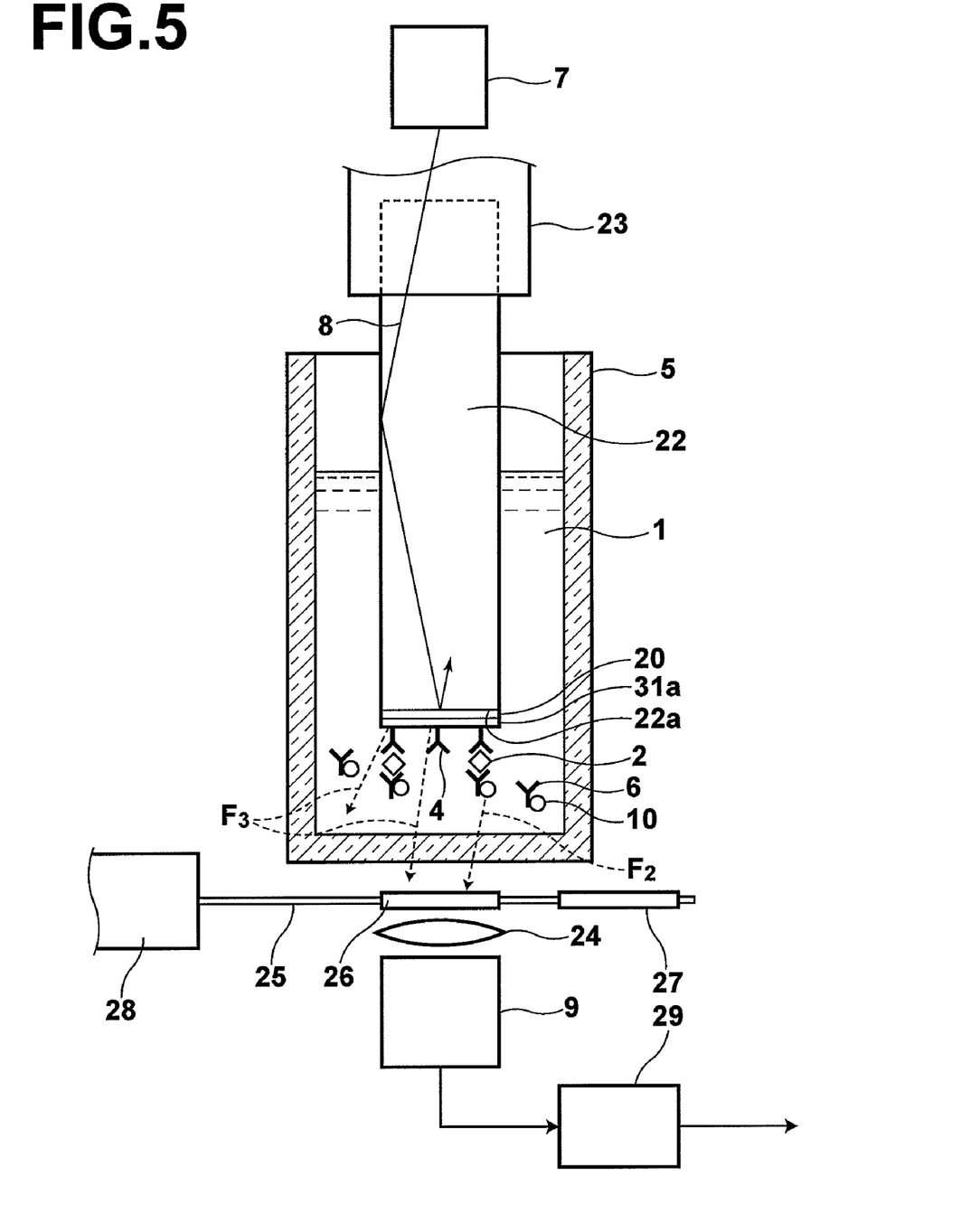
FIG. 5 is a schematic side view showing a third embodiment of the surface plasmon enhanced fluorescence sensor in accordance with the present invention.
Figure 6:
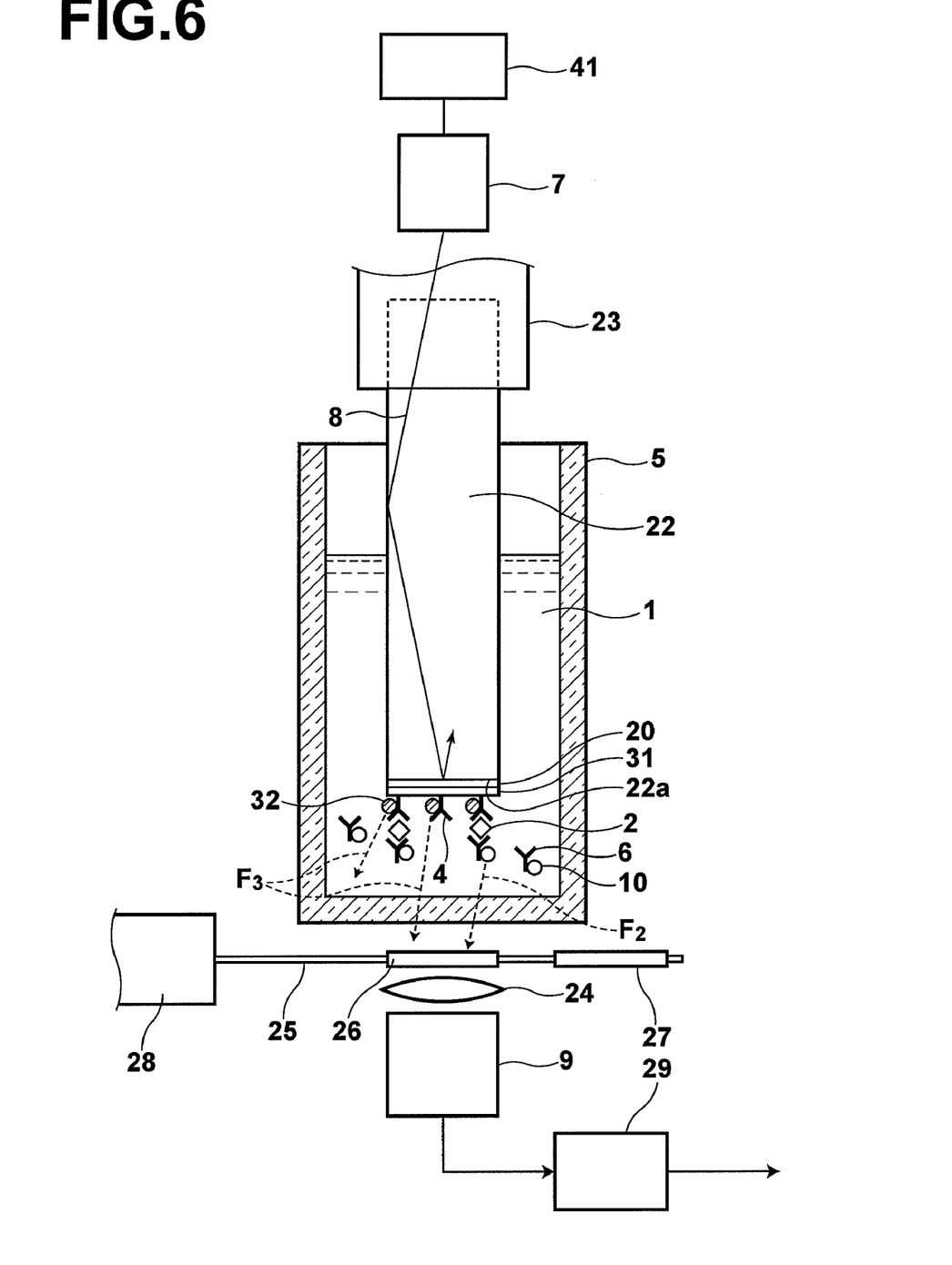
FIG. 6 is a schematic side view showing a fourth embodiment of the surface plasmon enhanced fluorescence sensor in accordance with the present invention.

The fluorescence detecting system described above is capable of being employed also in cases where the constitution illustrated in each of FIGS. 4, 5, and 6 is employed as the constitution for producing the reference fluorescence $F_3$.

In each of the embodiments described above, the reference fluorescent substance for producing the reference fluorescence $F_3$ is fixed to a part of the apparatus. Alternatively, instead of the reference fluorescent substance being fixed to a part of the apparatus, the reference fluorescent substance may be mixed in the liquid-state sample and may be utilized in this state for producing the reference fluorescence $F_3$.

What is claimed is:

1. A surface plasmon enhanced fluorescence sensor, comprising:
   i) an exciting light source, which produces exciting light having a predetermined wavelength $\lambda_1$,
   ii) a dielectric material block, which has been formed from a material capable of transmitting the exciting light,
   iii) a metal film, which has been formed on one surface of the dielectric material block,
   iv) a sample support section for supporting a sample at a position in the vicinity of the metal film,
   v) an exciting light irradiating optical system for irradiating the exciting light through the dielectric material block toward an interface between the dielectric material block and the metal film, such that total reflection conditions may be satisfied, and
   vi) analysis fluorescence detecting means for detecting an intensity of analysis fluorescence having a wavelength $\lambda_2$ and having been produced by an analysis fluorescent substance, which is contained in the sample, the analysis fluorescent substance producing the analysis fluorescence by being excited by an evanescent wave oozing out from the interface at the time at which the exciting light has impinged upon the interface,
   wherein the improvement comprises the provision of:
   a) a reference fluorescent substance, which is different from the analysis fluorescent substance and has been located at a position for excitation by the exciting light,
   b) reference fluorescence detecting means for detecting an intensity of reference fluorescence having a wavelength $\lambda_3$ and having been produced by the reference fluorescent substance, where $\lambda_3 \neq \lambda_2$, and c) operation processing means for normalizing the intensity of the analysis fluorescence, which has been detected by the analysis fluorescence detecting means, in accordance with the intensity of the reference fluorescence, which has been detected by the reference fluorescence detecting means.

2. A surface plasmon enhanced fluorescence sensor as defined in claim 1 wherein single common photo detecting means is used as the analysis fluorescence detecting means and the reference fluorescence detecting means, and the surface plasmon enhanced fluorescence sensor further comprises:

a first filter for transmitting the analysis fluorescence having the wavelength $\lambda_2$ and blocking the reference fluorescence having the wavelength $\lambda_3$, a second filter for blocking the analysis fluorescence having the wavelength $\lambda_2$ and transmitting the reference fluorescence having the wavelength $\lambda_3$, and filter changeover means, which is capable of selectively locating either one of the first filter and the second filter at a stage previous to the single common photo detecting means.

3. A surface plasmon enhanced fluorescence sensor as defined in claim 2 wherein a binding substance, which is capable of undergoing binding with a specific substance contained in the sample, has been fixed to a surface of the metal film, and the reference fluorescent substance has been fixed to the binding substance having been fixed to the surface of the metal film.

4. A surface plasmon enhanced fluorescence sensor as defined in claim 3 wherein the binding substance, which is capable of undergoing the binding with the specific substance contained in the sample, is an antibody, which is capable of undergoing the binding with an antigen contained in the sample.

5. A surface plasmon enhanced fluorescence sensor as defined in claim 2 wherein a specific film has been formed on a surface of the metal film, and the reference fluorescent substance has been fixed to the specific film.

6. A surface plasmon enhanced fluorescence sensor as defined in claim 5 wherein the specific film is an inflexible film constituted of a hydrophobic material.

7. A surface plasmon enhanced fluorescence sensor as defined in claim 1 wherein two independent photo detecting means are used as the analysis fluorescence detecting means and the reference fluorescence detecting means, and the surface plasmon enhanced fluorescence sensor further comprises an optical element for causing the analysis fluorescence having the wavelength $\lambda_2$ to travel toward the analysis fluorescence detecting means, and causing the reference fluorescence having the wavelength $\lambda_3$ to travel toward the reference fluorescence detecting means.

8. A surface plasmon enhanced fluorescence sensor as defined in claim 7 wherein a binding substance, which is capable of undergoing binding with a specific substance contained in the sample, has been fixed to a surface of the metal film, and the reference fluorescent substance has been fixed to the binding substance having been fixed to the surface of the metal film.

9. A surface plasmon enhanced fluorescence sensor as defined in claim 8 wherein the binding substance, which is capable of undergoing the binding with the specific substance contained in the sample, is an antibody, which is capable of undergoing the binding with an antigen contained in the sample.

10. A surface plasmon enhanced fluorescence sensor as defined in claim 7 wherein a specific film has been formed on a surface of the metal film, and the reference fluorescent substance has been fixed to the specific film.

11. A surface plasmon enhanced fluorescence sensor as defined in claim 10 wherein the specific film is an inflexible film constituted of a hydrophobic material.

12. A surface plasmon enhanced fluorescence sensor as defined in claim 1 wherein a binding substance, which is capable of undergoing binding with a specific substance contained in the sample, has been fixed to a surface of the metal film, and the reference fluorescent substance has been fixed to the binding substance having been fixed to the surface of the metal film.

13. A surface plasmon enhanced fluorescence sensor as defined in claim 12 wherein the binding substance, which is capable of undergoing the binding with the specific substance contained in the sample, is an antibody, which is capable of undergoing the binding with an antigen contained in the sample.

14. A surface plasmon enhanced fluorescence sensor as defined in claim 1 wherein the reference fluorescent substance has been fixed to a region of the dielectric material block.

15. A surface plasmon enhanced fluorescence sensor as defined in claim 1 wherein a specific film has been formed on a surface of the metal film, and the reference fluorescent substance has been fixed to the specific film.

16. A surface plasmon enhanced fluorescence sensor as defined in claim 15 wherein the specific film is an inflexible film constituted of a hydrophobic material.

17. A surface plasmon enhanced fluorescence sensor as defined in claim 1 wherein the reference fluorescent substance has been mixed in the sample.

18. A surface plasmon enhanced fluorescence sensor as defined in claim 1 wherein the fluorescence, which is produced by the reference fluorescent substance through multiphoton absorption, is employed as the reference fluorescence.

* * * * *